United States Patent [19]

Mumick et al.

[11] Patent Number: 5,969,052
[45] Date of Patent: Oct. 19, 1999

[54] TEMPERATURE SENSITIVE POLYMERS AND WATER-DISPERSIBLE PRODUCTS CONTAINING THE POLYMERS

[75] Inventors: Pavneet Singh Mumick; Yihua Chang; James Hongxue Wang, all of Appleton, Wis.

[73] Assignee: Kimberly Clark Worldwide, Inc., Neenah, Wis.

[21] Appl. No.: 08/778,724

[22] Filed: Dec. 31, 1996

[51] Int. Cl.⁶ .................................................. C08F 8/32
[52] U.S. Cl. .................................... 525/329.9; 525/330.1
[58] Field of Search ............................ 525/329.9, 330.1

[56] References Cited

U.S. PATENT DOCUMENTS

| | | | |
|---|---|---|---|
| 3,203,935 | 8/1965 | Miranda et al. | 260/78.5 |
| 3,897,404 | 7/1975 | Korte et al. | 260/79.5 NV |
| 4,002,171 | 1/1977 | Taft | 128/284 |
| 4,096,325 | 6/1978 | Teng et al. | 536/91 |
| 4,309,469 | 1/1982 | Varona | 428/74 |
| 4,537,807 | 8/1985 | Chan et al. | 428/74 |
| 4,870,137 | 9/1989 | Lopez et al. | 525/329.9 |
| 5,196,470 | 3/1993 | Anderson et al. | 524/379 |
| 5,252,332 | 10/1993 | Goldstein | 428/402 |
| 5,377,688 | 1/1995 | Besecke et al. | 525/330.5 |
| 5,395,897 | 3/1995 | Hurlock et al. | 525/344 |
| 5,464,545 | 11/1995 | Isharani et al. | 252/8.6 |
| 5,509,913 | 4/1996 | Yeo | 604/364 |
| 5,576,364 | 11/1996 | Isaac et al. | 524/80 |
| 5,728,207 | 3/1998 | Arfaei et al. | 106/709 |

FOREIGN PATENT DOCUMENTS

WO 97/24150  7/1997  WIPO.

OTHER PUBLICATIONS

Wu et al., "Synthesis and Charaterization of Thermally–Reversible Macroporous Poly(N–Isopropylacrylamide Hydrogels", *Journal of Polymer Science: Part A: Polymer Chemistry*, vol. 30, pp. 2121–2129 (1992), The month in the date of the publication is not available.

Ferruti et al., "Polymeric Acrylic and Methacrylic Esters and Amides by Reaction of Poly(acrylic Acid) and Poly-(methacrylic Acid) with N,N'–Carbonyl–diimidazole and Alcohols or Amines", *Journal of Polymer Science: Polymer Chemistry Edition*, vol. 13, pp. 2859–2862 (1975), The month in the date of the publication is not available.

Kurahashi et al., "Preparation and Properties of a New Temperature–Sensitive Ionized Gel", *Journal of Chemical Engineering of Japan*, vol. 26, No. 1, pp. 89–93 (1993), The month in the date of the publication is not available.

Kabra et al., "Synthesis of fast response, temperature–sensitive poly(N–isopropylacrylamide) gel", *Polymer Communications*, vol. 32, No. 11, pp. 322 and 323 (1991), The month in the date of the publication is not available.

Okuyama et al., "Swelling controlled zero order and sigmoidal drug release from thermo–responsive poly(N–isoproplacrylamide–co–butyl methacrylate) hydrogel", *J. Biomater. Sci. Polymer Edn*, vol. 4, No. 5, pp. 545–556 (1993), The month in the date of the publication is not available.

Nagaoka et al., "Synthesis of Poly9N–isopropylacrylamide) Hydrogels by Radiation Polymerization and Cross–Linking", *Macromolecules*, vol. 26, No. 26, pp. 7386–7388, The date of publication is not available.

Takeuchi et al., "Microspheres prepared with a temperature–responsive macromonomer", *Makromol. Chem.*, vol. 194, pp. 551–558 (1993), The month in the date of the publication is not available.

Database WPI, Derwent Info. Ltd., London, JP 63117016 (Agency of Ind. Sci. & Techn.), May 21, 1988 (Abstract).

Database WPI, Derwent Info. Ltd., London, JP 63117017 (Agency of Ind. Sci. & Techn.), May 21, 1988 (Abstract).

Database WPI, Derwent Info. Ltd., London, JP 58174408 (Agency of Ind. Sci. & Techn.), Oct. 13, 1983 (Abstract).

Database WPI, Derwent Info. Ltd., London, JP 6233809 (Kubota Y), Aug. 23, 1994 (Abstract).

Database WPI, Derwent Info. Ltd., London, JP 5125123 (Lion Corp.), May 21, 1993 (Abstract).

Hartmann et al., "Polymeric Herbicides", *Polymer Bulletin*, vol. 13, pp. 195–200 (1985), The month in the date of the publication is not available.

Chen et al., "Synthesis of carboxylated poly(NIPAAm) oligomers and their application to form thermo–reversible polymer–enzyme conjugates", *J. Biomater. Sci. Polymer Edn*, vol. 5, No. 4, pp. 371–382 (1994), The month in the date of the publicaton is not available.

Database Dialog, Patent Information Organization, JP 59076044 (Arakawa Chem. Ind. Co. Ltd.), Apr. 28, 1984 (Abstract).

Database Dialog, Patent Information Organization, JP 53007615 (Kohjin Co. Ltd.), Jan. 24, 1978 (Abstract).

*Primary Examiner*—Ana Woodward
*Attorney, Agent, or Firm*—Jones & Askew, LLP

[57] ABSTRACT

The present invention is directed to a novel process of making N-isopropyl acrylamide (NiPAm) polymers based upon the reaction of poly(acrylic acid) and N-isopropylamine. The disclosed method of the present invention uses polyacrylic acid as a starting material to synthesize NiPAm polymers. In one embodiment, the present invention discloses a condensation reaction of an intermediate salt to form homopolymers, copolymers and terpolymers of N-isopropyl acrylamide (NiPAm) with acrylic acid and/or alkyl acrylates in a molten state, which is adaptable to a continuous reactive extrusion process. Binder compositions, water-dispersible products and thermoformable articles containing the NiPAm polymers are also disclosed.

27 Claims, No Drawings

TEMPERATURE SENSITIVE POLYMERS AND WATER-DISPERSIBLE PRODUCTS CONTAINING THE POLYMERS

FIELD OF THE INVENTION

The present invention is directed to a novel process of making N-isopropyl acrylamide (NiPAm) polymers, including, but not limited to, homopolymers, copolymers and terpolymers, from polyacrylic acid. In addition, the present invention is directed to temperature responsive binders comprising N-isopropyl acrylamide (NiPAm) polymers alone or with at least one hydrophobic polymer. The present invention is also directed to thermoformable articles comprising N-isopropyl acrylamide (NiPAm) polymers. Moreover, the present invention is directed to water-dispersible products, including flushable products such as diapers, tampons, feminine pads, pantiliners, etc., which contain a temperature responsive binder and/or thermoformable articles comprising N-isopropyl acrylamide (NiPAm) polymers.

BACKGROUND OF THE INVENTION

NiPAm polymers, including homopolymers, copolymers and terpolymers or higher containing N-isopropyl acrylamide structural units, are temperature responsive polymers due to their Lower Critical Solution Temperature, or LCST. As used herein, the term "LCST" describes the temperature at which the polymer solution experiences a phase transition going from one phase (homogeneous solution) to a two-phase system (a polymer rich phase and a solvent rich phase) as the solution temperature increases. These materials remain relatively inert in warm water or synthetic urine (greater than about 28° C.), but disperse quickly in cold water (less than about 25° C.) with immediate loss in mechanical strength. It has been discovered that due to their inverse solubility, these temperature-triggered materials are particularly useful in water-dispersible products, most particularly flushable personal care products such as diapers, tampons, feminine pads, pantiliners, etc. As used herein, the term "water-dispersible product" means a product which, when exposed to a fluid at a temperature of approximately 22° C. for approximately 2 minutes, dissolves or fragments into pieces all of which pass through a 20 mesh screen.

The conventional synthesis of NiPAm polymers requires the use of an expensive and not readily available monomer, N-isopropyl acrylamide. Temperature responsive, N-isopropyl acrylamide polymers and copolymers are known to be synthesized by free-radical polymerization of N-isopropyl acrylamide or copolymerization of N-isopropyl acrylamide with another monomer. For example, polymerization reactions of (N-isopropyl acrylamide) in benzene (JP 63117016) and ethyl acetate (JP 63117017) are known. Crosslinked poly(N-isopropyl acrylamide) hydrogels are prepared by radiation polymerization of N-isopropyl acrylamide as disclosed in *Macromolecules,* 26(26), 7386 (1993). Similar hydrogels are also synthesized by copolymerization of N-isopropyl acrylamide and methylene bisacrylamide under various conditions. (See *Polym. Commun.,* 32(11), 322 (1991); *J. Polym. Sci., Part A: Polym. Chem.,* 30(10), 2121 (1992).

A number of random, block or graft copolymers containing N-isopropyl acrylamide monomer units have been synthesized by various polymerization methods. For instance, a number of monomers including butyl methacrylate, N-isopropyl methacrylamide and dextran sulfate have been polymerized with N-isopropyl acrylamide to prepare random copolymers (*J. Chem. Eng. Jpn.,* 26(1), 89 (1993); *J. Biomater. Sci., Polym. Ed.,* 5(4), 371 (1994); JP 58174408; JP 58215413)). Hoffman et al. synthesized carboxyl terminated poly(N-isopropyl acrylamide) oligomers, which were then reacted with biopolymers to form thermo-reversible polymer-enzyme conjugates (*J. Biomater. Sci., Polym. Ed.,* 4(5), 545 (1993)). Furthermore, poly(N-isopropyl acrylamide) macromonomers have been synthesized and subsequently polymerized with other vinyl monomers to yield temperature-responsive copolymers (*Makromol. Chem.,* 194(2), 551 (1993)).

The synthesis of a number of polymers, which do not contain N-isopropyl acrylamide monomer units, particularly polymethacrylamides, by amidation of polymeric acyl chloride is described in *Makromol. Chem.,* 194(2), 363 (1993). This article discloses that poly(acrylic acid) reacts in either aqueous or organic media with low molecular weight amines and polymeric amines to produce polyamides. For example, poly(acrylic acid) is reacted with perfluoroalkylamines to give polymers having a degree of amidation of 4–100% (JP 03243609). DE 3700518 discloses poly(acrylic acid) in aqueous solution treated with long chain alkyl amines to prepare partially amidated polymers. Amidation of poly (acrylic acid) is further disclosed in the following references: *Yakhak Hoechi,* 30(5), 232 (1986); JP 60079013; *Polym. Bull.,* 13(3), 195 (1985); DE 3009235; DE 2533443; *J. Polym. Sci., Polym. Chem. Ed.,* 13(12), 2859 (1975); *Eur. J Biochem.,* 17(3), 561 (1970).

Poly(N-isopropyl acrylamide) (PNiPAm) exhibits a cloud point or inverse solubility property, i.e. the polymer is soluble in water below about 34° C. and insoluble above that temperature. Poly(N-isopropyl acrylamide) (PNiPAm) has been cited in several patents where its temperature sensitive properties have been utilized. N-substituted polyacrylamides have been proposed for wound dressings with good absorbing characteristics and easy removal from the wound surface (JP 6233809). Further, flexible laminated films for control of light transmission have been disclosed with PNiPAm (JP 5177757). U.S. Pat. No. 5,509,913 describes the potential use of conventional PNiPAm for applications in flushable personal care products. Two related patents, JP 58174408 and JP 84042005, assigned to the Agency of Industrial Science and Technology, disclose copolymers of N-isopropyl acrylamide and N-isopropyl methacrylamide and the use of these copolymers as aqueous adhesives and coatings.

Other temperature-responsive polymers are described. For example, U.S. Pat. No. 5,509,913, mentioned above, covers a broad range of temperature and ion sensitive polymers. Stafford et al. describes the use of hydroxypropylcellulose (HPC) as a temperature sensitive binder in *J. Pharm. Pharmacol.* (1978), 30(1), 1. Also, a salt sensitive water soluble polyurethane binder for flushable nonwoven fabrics is disclosed in U.S. Pat. No. 4,002,171, issued to Taft. Further, a salt sensitive water soluble terpolymer for making flushable paper diapers, bandages and sanitary towels is disclosed in Japanese Patent No. JP 5125123 and U.S. Pat. No. 5,312,883 assigned to LION Corp.

What is needed in the art is an inexpensive and environmentally safe way to produce NiPAm polymers for use as binder materials and thermoformable articles that readily disperse in cold water, but remain structurally sound in warm water. Moreover, a method of producing NiPAm polymers having tailored cloud points (i.e., specific cloud points within a desired temperature range) is also needed.

SUMMARY OF THE INVENTION

The present invention is directed to a novel process of making N-isopropyl acrylamide (NiPAm) polymers comprising the reaction of poly(acrylic acid) and N-isopropylamine. The disclosed method of the present invention uses polyacrylic acid as a starting material to synthesize NiPAm polymers, not the expensive monomer, (N-isopropyl acrylamide), as is conventionally taught in the prior art. In one embodiment, the present invention discloses a condensation reaction of an intermediate salt to form homopolymers, copolymers and terpolymers of N-isopropyl acrylamide (NiPAm) with acrylic acid and/or alkyl acrylates in a molten state, which is adaptable to a continuous reactive extrusion process.

The present invention is further directed to a binder material for binding fibrous material into an integral structure, wherein the binder material includes the above-mentioned NiPAm homopolymer, copolymer or terpolymer. Moreover, the present invention is directed to water-dispersible fibrous substrates comprising at least one fibrous material and a binder material for binding the fibrous material into an integral structure, wherein the binder material includes the above-mentioned NiPAm homopolymer, copolymer or terpolymer. Furthermore, the present invention is directed to thermoformable articles comprising the above-mentioned N-isopropyl acrylamide polymers. Such articles can be in the form of fibers, films or fabrics and find applicability in a variety of consumer products.

In addition, the present invention is directed to the incorporation of the above-mentioned binders and thermoformable articles in products used to retain fluids exuded from the body such as blood, menstrual fluid and urine. Specifically, the binders and thermoformable articles of the present invention are useful in connection with a variety of water-dispersible products, and especially absorbent products such as sanitary napkins, diapers, dressings and the like. The articles of the present invention exhibit adequate tensile strength and retain their structural integrity when in contact with the aforesaid body fluids, yet are readily dispersible in water so that the absorbent product may be flushed away after use.

Fabrics are widely used as components of such disposable goods as sanitary napkins, diapers, bandages, and the like. Such fabrics, if they are to function effectively, must maintain their structural integrity, as well as exhibit satisfactory tensile strength, when they are wet or damp with various body fluids such as blood, menstrual fluid and urine, with which they come into contact during use. It has been recognized that if such fabrics, while retaining their strength in body fluids, were to lose substantially all their tensile strength when exposed to water and become readily dispersible therein, disposal problems would be substantially eliminated since the fabrics could be easily and conveniently disposed of by contacting the fabric with water. The present invention provides another mechanism for eliminating disposal problems associated with various consumer products.

DETAILED DESCRIPTION OF THE INVENTION

Unlike conventional methods of making NiPAm polymers, the present invention discloses a novel reaction process, which uses the amidation reaction of a low-cost and abundant raw material, polyacrylic acid, to produce PNiPAm and its copolymers and terpolymers. The synthesis of N-isopropyl acrylamide structural units is actually performed on the polymer backbone of polyacrylic acid, eliminating the need for expensive starting materials such as N-isopropyl acrylamide. Another advantage of the disclosed process is that copolymers, terpolymers or multipolymers of various compositions can be readily produced by using active-hydrogen-containing compounds such as alcohols and amines instead of the individual monomers. Furthermore, the PNiPAm, copolymers and terpolymers made by the disclosed method do not contain residual monomers. Therefore, the safety and environmental concerns associated with conventional production of N-isopropyl acrylamide polymers are largely eliminated.

The present invention also improves and expands the applicability of PNiPAm and its inverse solubility property by (1) polymerizing NiPAm with one or more various monomers to adjust the cloud point and increase dehydration above the cloud point, and (2) blending PNiPAm, or its copolymer or terpolymer, with at least one hydrophobic polymer to increase dehydration above the cloud point. The resulting copolymers, terpolymers and blends have been found to have previously undiscovered applications. One preferred application of the disclosed formulations is as a water-dispersible binder.

The present invention discloses a variety of formulations with applicability as water-dispersible temperature sensitive binders, including a preferred binder formulation comprising a copolymer containing N-isopropyl acrylamide and N-tert-butylacrylamide (TBAM) structural units and another preferred binder formulation comprising a N-isopropyl acrylamide polymer and polyvinyl acetate (PVAc) as the at least one hydrophobic polymer, resulting in a smoother, softer binder with a substantial cost saving.

Desirably, a temperature responsive polymer for use as a binder in water-dispersible products has the following properties: (1) the polymer remains dehydrated above the cloud point, i.e. the polymer rich phase has only small amounts of solvent; (2) the polymer has extremely small amounts of polymer in solution above the cloud point, i.e. the solvent rich phase is essentially all solvent; and (3) the polymer has a cloud point between about 20 to 40° C., more desirably between about 20 to 30° C., and most desirably between about 21 to 25° C., such that, the polymer stays insoluble while in-use (i.e., when it is close to the body) and dissolves or disperses in an aqueous solution when the temperature is below the cloud point, e.g. during flushing.

The present invention discloses a method of making polymers, copolymers and terpolymers containing the N-isopropyl acrylamide structural unit and the use of such polymers as binder materials and thermoformable articles in water-dispersible products, and especially, flushable personal care products. Polyacrylic acid or polymethacrylic acid resins of average molecular weight ranging from about 2,000 to about 5,000,000 grams/mole are the preferred starting materials for the reaction method of the present invention. The preferred range of molecular weight depends on the intended end use or application of the poly(N-isopropyl acrylamide) (PNiPAm) produced. For example, for fiber applications, a melt flow index of about 10 to 1,000 g/10 min. at about 230° C. or a similar extrusion temperature is desired. For film applications, a melt flow index from about 0.1 to 20 grams/10 min. at about 230° C. or a similar extrusion temperature is desired so as to provide melt extrusion properties required in film-making processes.

There are several ways to carry out the present invention. A first desirable version of the reaction process of the present invention comprises of a two-step process. In the first step, polyacrylic acid is reacted with isopropylamine without solvent or with a polar solvent. Suitable polar solvents include, but are not limited to, water, methanol, and ethanol. Upon the reaction between the components, isopropylammonium polyacrylate salt is produced. The salt is subsequently isolated and purified to be free of solvent and unreacted amine.

In the second step, the salt is then added to a melt reaction device, such as a resin kettle or a twin-roller melt mixer, to conduct a condensation reaction. The by-product, water, can be evacuated in order to increase the conversion to PNiPAm.

Another desirable version of the reaction process of the present invention is a continuous process. Polyacrylic acid, having a desirable molecular weight of between about 2000 and 5,000,000 and a desirable melt flow index of between about 0.1 to 500 g/10 min. at about 230° C., is fed to the extruder. Upon melting of the polymer, a stream of isopropylamine is injected into the melt phase of the polyacrylic acid to produce an intermediate salt at the end of a first reaction zone of the extruder. Upon further extrusion, the polymeric salt decomposes into poly(N-isopropyl acrylamide) (PNiPAm) and water. The water is then evacuated from a last section of the extruder. By controlling the extrusion conditions, including screw configuration, extrusion rate, screw speed, reaction temperature and temperature profile, poly(N-isopropyl acrylamide) or a copolymer of isopropyl acrylamide and acrylic acid of various compositions can be produced by the process.

In a further variation of the above continuous process, an aliphatic alcohol or a mixture of various alcohols can also be injected into the extruder during the continuous process to synthesize a copolymer or terpolymer of isopropyl acrylamide and at least one alkyl acrylate. The presence of alkyl acrylate groups in the NiPAm polymer provides a way to control the cloud point or the trigger temperature of the NiPAm polymer. For example, the incorporation of hydrophobic alkyl acrylate groups causes the cloud point to decrease. The relative amount of NiPAm to alkyl acrylate groups determines the magnitude of the cloud point reduction.

A desirable group for copolymerization with NiPAm is N-tert-butylacrylamide (TBAM). By injecting N-tert-butyl amine into the reaction mixture during the continuous extrusion process, polymers containing NiPAm and TBAM structural units are produced. When NiPAm is copolymerized with up to about 20 mole % N-tert-butylacrylamide (TBAM), the resulting copolymer becomes more inert to warm water relative to the homopolymer of N-isopropyl acrylamide. On copolymerization of NiPAm with about 0–20 mole % of N-tert-butylacrylamide (TBAM), the cloud point of the copolymer can be reduced to a desired target range of between about 20 to 40° C., more desirably between about 20 to 30° C., and most desirably between about 21 to 25° C., with better dehydration above the cloud point since TBAM is relatively more hydrophobic than PNiPAm. Table 1 below illustrates the relationship between the degree of NiPAm copolymerization with TBAM and the trigger temperature of the binder material. When these copolymer solutions are applied as binder materials to a fibrous substrate, the binder materials remain stable in warm water, but disperse within 10 seconds in cold water with agitation.

TABLE I

Effect of Mole % TBAM on Cloud Point and Trigger Temperature of the Binder

| Mole % TBAM | Cloud Point (°C.) | Trigger Temp. (°C.) |
|---|---|---|
| 0 | 34.0 | 33.5 |
| 4 | 32.0 | 31.5 |
| 8 | 29.0 | 28.5 |

When NiPAm polymers are blended with at least one hydrophobic polymer, such as 0–60 wt % poly(vinyl acetate) (PVAc), the resulting blend becomes more inert to warm water relative to the NiPAm polymer alone. To illustrate the effect of adding at least one hydrophobic polymer to the poly(N-isopropyl acrylamide) (PNiPAm) binder material, PNiPAm was blended with poly(vinyl acetate) (PVAC) from a common solvent, methanol. The PVAc was desirably surfactant-free so that surfactant would not interact with PNIPAm, hydrating the polymer above the cloud point or elevating the cloud point itself depending on the type of surfactant. A suitable PVAc is VINAC® B-15 from Air Products and Chemicals, Inc., Allentown, Pa.

Table II below illustrates the effect of PVAc on the dispersal time of a fibrous substrate with 20–25 weight percent add-on of a 3 to 3.5 wt % solution of PNiPAm/PVAc in methanol applied to a fibrous substrate. All of the fibrous substrates retained their integrity in warm water (>34° C.), but dispersed in cold water (<33.5° C.) in the times specified below. As shown in Table II, the trigger temperature remained unaffected when using the homopolymer of PNiPAm with PVAc since temperature triggering is determined by the PNiPAm part of the binder formulation. As shown above, one can adjust the trigger temperature by copolymerizing PNiPAm with monomers, such as TBAM.

TABLE II

Effect of Blended PVAc on Trigger Temperature and Time to Disperse below the Trigger Temperature

| Wt % PVAc | Trigger Temp. (°C.) in Cold Water (sec) | Dispersal Time |
|---|---|---|
| 0 | 33.5 | 10 |
| 30 | 33.5 | 10 |
| 50 | 33.5 | 20 |
| 60 | 33.5 | 60 |

To disperse the binder slower than the times indicated in Table II, one can add up to about 70 wt % PVAc and still achieve dispersibility. Binders containing PVAc have a smoother feel due to the lower $T_g$ (~29° C.) of PVAc relative to that of PNiPAm (~140 C.).

The reaction method of the present invention is not limited to the compositions above. Other suitable monomers in the NiPAm polymers include, but are not limited to, alkyl acrylates and alkyl methacrylates. The choice of suitable monomers and the degree of polymerization is not limited, as long as the resulting copolymer or terpolymer possesses binder properties (i.e., inverse solubility, dispersibility in cold water, etc.) suitable for use in water-dispersible products. Desirably, the amount of NiPAm monomer in the copolymers of the present invention is from about 50 to about 100 mole percent based on the total moles of the monomer structural units. Most desirably, the amount of NiPAm monomer in the copolymer is from about 70 to about 90 mole percent based on the total moles of the monomer structural units.

Further, the present invention encompasses a variety of blends comprising one or more NiPAm polymers with one or more hydrophobic polymers. Other suitable hydrophobic polymers for blending with the one or more NiPAm polymers include, but are not limited to, polystyrene, styrene-acrylonitrile copolymer, acrylonitrile-butadiene-styrene terpolymer, ethylene-acrylic acid copolymer, ethylene-methacrylic acid copolymer, polyolefins grafted with polar functional groups such as acrylic acid, maleic anhydride, etc., polyacrylates, polymethacrylates, polyvinyl butyral, polyurethanes, polyesters, polyamides, polyethylene vinyl acetate, and ethylene-vinyl alcohol copolymer. The choice and number of suitable hydrophobic polymers to be blended with the NiPAm polymer or polymers is not limited, as long as the resulting blend possesses binder properties (i.e., inverse solubility, dispersibility in cold water, etc.) suitable for use in water-dispersible products. Desirably, the amount of NiPAm polymer in the binder blend is from about 30 to about 99 weight percent based on the total weight of the polymer mixture in the binder composition. Most desirably, the amount of NiPAm polymer in the blend is from about 50 to about 99 weight percent based on the total weight of the polymer mixture in the binder composition.

The binder material of the present invention may contain other components in addition to the NiPAm polymer and the at least one hydrophobic polymer. In some embodiments, it may be desirable to employ one or more additives including, but not limited to, compatibilizers, processing aids, dispersants, slip agents, thickening agents, anti-foaming agents, and anti-microbial agents, as fabricating agents or as modifiers depending on the specific properties desired in the final product.

The NiPAm polymer binder compositions of the present invention are highly compatible with a great variety of plasticizers; thus such plasticizers may be incorporated therein to improve such binder composition characteristics as flexibility and resistance to abrasion. These properties are particularly important when the binder composition is used in connection with items to be in contact with human skin such as the aforementioned sanitary napkins, diapers and the like. For these purposes, water soluble plasticizers such as glycerol and polyethylene glycol can be used, as well as water-insoluble plasticizers such as castor oil, and the like.

The binder material of the present invention can be applied to any fibrous substrate. Fibrous substrates include, but are not limited to, nonwoven and woven fabrics. For water-dispersible, flushable products, most desirable substrates are nonwoven fabrics due to their permeability of fluids such as blood, urine and menses. As used herein, the term "nonwoven fabric" refers to a fabric that has a structure of individual fibers or filaments which are randomly interlaid in a mat-like fashion. Nonwoven fabrics can be made from a variety of processes including, but not limited to, air-laid processes, wet-laid processes, hydroentangling processes, staple fiber carding and bonding, and solution spinning.

The fibers forming the fabrics above can be made from a variety of materials including natural fibers, synthetic fibers, and combinations thereof. The choice of fibers depends upon, for example, fiber cost and the intended end use of the finished fabric. For instance, suitable fibrous substrates may include, but are not limited to, natural fibers such as cotton, linen, jute, hemp, cotton, wool, wood pulp, etc. Similarly, regenerated cellulosic fibers such as viscose rayon and cuprammonium rayon, modified cellulosic fibers, such as cellulose acetate, or synthetic fibers such as those derived from polyesters, polyamides, polyacrylics, etc., alone or in combination with one another, may likewise be used. Blends of one or more of the above fibers may also be used if so desired.

The fiber length is important in producing the fabrics of the present invention. The minimum length of the fibers depends on the method selected for forming the fibrous substrate. For example, where the fibrous substrate is formed by carding, the length of the fiber should usually be at least about 20 mm, and desirably about 25 to 40 mm, to insure uniformity. Where the fibrous substrate is formed by air-laid or wet-laid processes, the desired fiber length is less than about 15 mm. Fibers having a length of greater than 50 mm are within the scope of the present invention. However, for some embodiments, such as water-dispersible flushable products, it has been determined that when a substantial quantity of fibers having a length greater than about 15 mm is placed in the fabric, though the fibers will disperse and separate in water, their length tends to form "ropes" of fibers which is undesirable when flushing in home toilets. Therefore, for flushable products, it is desirable that the fiber length be 15 mm or less so that the fibers will not have a tendency to "rope" when they are flushed through a toilet. In most embodiments, fibers are of a length less than about 15 mm so that the fibers disperse easily from one another when in contact with water, desirably ranging from about 6 to about 15 mm in length.

It has been found that nonwovens formed from natural fibers, alone or in combination with at least one of polyolefin, polyester and polyamide fibers, are particularly well-suited for the above applications.

The fibrous substrate of the present invention may be formed from a single layer or multiple layers. In the case of multiple layers, the layers are generally positioned in a juxtaposed or surface-to-surface relationship and all or a portion of the layers may be bound to adjacent layers. The nonwoven web may also be formed from a plurality of separate nonwoven webs wherein the separate nonwoven webs may be formed from single or multiple layers. In those instances where the nonwoven web includes multiple layers, the entire thickness of the nonwoven web may be subjected to a binder application or each individual layer may be separately subjected to a binder application and then combined with other layers in a juxtaposed relationship to form the finished nonwoven web.

The binder composition may be applied to the fibrous substrate by any known process of application. Suitable processes for applying the binder material include, but are not limited to, printing, spraying, impregnating or by any other technique. The amount of binder composition may be metered and distributed uniformly within the fibrous substrate or may be non-uniformly applied to the fibrous substrate. The binder composition may be distributed throughout the entire fibrous substrate or it may be distributed within a multiplicity of small closely spaced areas. Desirably, the binder composition is uniformly distributed within the fibrous substrate.

For ease of application to the fibrous substrate, the binder containing at least one NiPAm polymer and any additives may be dissolved in water, or in non-aqueous solvent such as methanol, ethanol, or the like, water being one desired solvent, to provide solutions containing up to about 30 percent by weight of binder composition solids, most desirably from about 6 to 20 percent by weight of binder composition solids. As discussed above, plasticizers, such as glycerol, polyethylene glycol, castor oil, and the like, may be added to the solution containing the binder composition, the amount of such plasticizers varying according to the softness desired in the final fabric. Also, perfumes, coloring agents, antifoams, bactericides, surface active agents, thickening agents, fillers and similar additives can be incorporated into the solution of binder components if so desired. Furthermore, other water soluble or water dispersible binding agents such as aqueous dispersions of, for example, polyvinyl alcohol, polyvinyl chloride, polyvinyl acetate, polyacrylates, polymethacrylates, copolymers of acrylates and methacrylates, copolymers of vinyl acetate with ethylene, acrylates and/or methacrylates and copolymers of acrylates and/or methacrylates with vinyl chloride can also be added to the binder composition solution in order to obtain bonded fabrics having various desired properties.

Once the binder composition is applied to the substrate, the substrate is dried by any conventional means. Once dry, the coherent fibrous substrate exhibits improved tensile strength when compared to the tensile strength of the untreated wet-laid or dry-laid substrates, and yet has the ability to rapidly "fall apart", or disintegrate when placed in cold water and agitated. For example, the tensile strength of the fibrous substrate may be increased by at least 25 percent as compared to the tensile strength of the untreated substrate not containing the binder. More particularly, the tensile strength of the fibrous substrate may be increased by at least 100 percent as compared to the tensile strength of the untreated substrate not containing the binder. Even more particularly, the tensile strength of the fibrous substrate may be increased by at least 500 percent as compared to the tensile strength of the untreated substrate not containing the binder.

A desirable feature of the present invention is that the improvement in tensile strength is effected where the amount of binder composition present, "add-on", in the resultant fibrous substrate represents only a small portion, by weight of the entire substrate. The amount of "add-on" can vary for a particular application; however, the optimum amount of "add-on" results in a substrate which has integrity while in use and also quickly disperses when agitated in water. For example, the binder components typically are up to about 60 percent, by weight, of the total weight of the substrate. More particularly, the binder components may be up to about 40 percent, by weight, of the total weight of the substrate. Even more particularly, the binder components may be up to about 25 percent, by weight, of the total weight of the substrate.

As with the amount of "add-on", the density of the resulting fiber substrate should be such that the substrate maintains structural integrity while in use, but quickly disperse when agitated in water. Although the density may vary for a given application, generally the fiber substrate will desirably have a density up to about 0.4 grams per cubic centimeter, more desirably of about 0.01 to 0.3 grams per cubic centimeter, and most desirably a density of about 0.025 to about 0.2 grams per cubic centimeter.

In another embodiment of the present invention, thermoformable articles are formed from at least one NiPAm polymer produced by the above-mentioned extrusion method. The thermoformable articles may be in the form of single or multiple layer articles wherein at least one layer comprises the NiPAm polymer in the form of individual fibers, a film or a fabric. The thermoformable articles are also useful in a variety of consumer products, especially water-dispersible products.

The binder materials of the present invention may be incorporated into any water-dispersible product, and especially body fluid absorbent products such as sanitary napkins, diapers, surgical dressings and the like. These products generally include an absorbent core, comprising one or more layers of an absorbent material. The core may also comprise one or more layers of a fluid-pervious element, such as fibrous tissue, gauze, plastic netting, etc. These are generally useful as wrapping materials to hold the components of the core together. Additionally, the core may comprise a fluid-impervious element or barrier to preclude the passage of fluid through the core and on the outer surfaces of the product. Desirably, the barrier also is water-dispersible. A film of a NiPAm polymer having substantially the same composition as the aforesaid water-dispersible binder is particularly well-suited for this purpose. In accordance with the present invention, the NiPAm polymer composition is useful for forming each of the above-mentioned product components including the layers of absorbent core, the fluid-pervious element, the wrapping materials, and the fluid-impervious element or barrier.

Those skilled in the art will readily understand that the water-dispersible products of the present invention may be advantageously employed in the preparation of a wide variety of absorbent personal care products designed to be contacted with body fluids. Such absorbent products may only comprise a single layer of the fibrous substrate or may comprise a combination of elements as described above. Although the fibrous substrate of the present invention is particularly suited for personal care products, the fibrous substrate of the present invention may be advantageously employed in the preparation of a wide variety of consumer products other than personal care products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

500 grams of polyacrylic acid having a weight average molecular weight of 450,000 grams/mole was dissolved in 700 milliliters of anhydrous ethanol. The mixture was heated to 60° C. while stirring. After the dissolution of polyacrylic acid, the solution was cooled to 30° C. A stoichiometric amount of isopropylamine was added dropwise. White precipitate was formed. The precipitate was collected and ethanol was removed under vacuum. The FT-IR analysis showed an isopropylammonium acrylate salt peak at 1540 $cm^{-1}$.

EXAMPLE 2

Since the degree of salt formation of poly(acrylic acid) with isopropylamine is affected by the polarity of solvent, the yield of the above reaction was examined in several solvents including water, water/methanol (30/70, v/v), methanol, isopropanol, and n-butanol in addition to ethanol as in Example 1. It was found that solvents with higher polarity such as water, methanol and ethanol gave nearly quantitative yields, whereas isopropanol only yielded 70% salt. n-Butanol could not completely dissolve polyacrylic acid; highly solvated polyacrylic acid residual was still visible after eight hours. When precipitated in tetrahydrofuran (THF), the salt from ethanol coagulated and easily separated from the solvent. The salt was more dispersed when precipitated from water or methanol. Therefore, ethanol was selected as a desired solvent for salt formation.

100 grams of polyacrylic acid (same source as in Example 1) was dissolved in 1.5 liters of ethanol. 125 grams of isopropylamine (1.5× excess) was added at once with vigorous stirring. A large amount of precipitate was formed. The solution was stirred under nitrogen for 24 hours. Most of the precipitate formed initially was redissolved in the ethanol. The salt was subsequently precipitated in 2 liters of THF and dried under vacuum. Analysis by both $^1H$ and $^{13}C$ nuclear magnetic resonance (NMR) spectroscopy indicated that the salt made by this procedure is 98% pure.

EXAMPLE 3

This example refers to a melt phase reaction of isopropylammonium polyacrylic acid salt in a Haake twin-roller mixer: Rheomix 600 using two roller blade-type rollers. 47 grams of isopropylammonium polyacrylate salt, as prepared in Example 2, was added to the mixer preheated at 180° C. Some resin in a form of foam escaped from the top closing block of the mixer. The reaction continued for 11 minutes at 150 rpm of roller speed. During the reaction, an initial exotherm caused the temperature to rise to 196° C. and subsequently drop back to 163° C.

Analysis by $^{13}$C-NMR showed that the resulting polymer had 43 weight percent N-isopropyl acrylamide derived structural units and 57 weight percent acrylic acid units.

EXAMPLE 4

This example refers to another melt phase reaction of isopropylammonium polyacrylic acid salt in a Haake twin-roller mixer: Rheomix 600 using two roller blade-type rollers. 42 grams of isopropylammonium polyacrylate salt, as prepared in Example 2, was added to the mixer preheated at 180° C. The sample chute was left on the mixer to prevent foam formation. Water, as a byproduct, was seen as white steam escaping from the mixer. The mixture was stirred at 150 rpm of roller speed for 20 minutes. The melt temperature increased to a peak of 192° C. and then dropped back to 155° C.

Analysis by $^{13}$C-NMR showed that the resulting polymer had 45 weight percent N-isopropyl acrylamide derived structural units and 55 weight percent acrylic acid units.

EXAMPLE 5

50 grams of N-isopropylammonium polyacrylate salt was placed in a 1 liter reaction kettle equipped with a mechanical stirrer, a thermometer, a nitrogen inlet, a nitrogen outlet, and a Dean-Stark trap with a condenser. The reaction temperature was kept at 150 to 180° C. for four hours during which 5.5 grams of water was collected. The collection trap was then replaced with a vacuum line and the reaction was continued for additional two hours. The theoretical amount of water for 100% conversion is 5.2 grams. The excess amount of liquid that was collected during the reaction is believe to have resulted from side reactions such as salt decomposition.

Analysis of the product by infrared spectroscopy showed 80 weight percent N-isopropyl acrylamide structural units and 20 weight percent acrylic acid units.

EXAMPLE 6

A 3 wt % aqueous solution of poly(N-isopropylacrylamide) (PNiPAm) was applied to a substrate using a wire-wound rod (#22) to provide a specific amount of add-on. The substrate was a wet-laid nonwoven made from 0.5", 3 denier fibers. The substrate had 60 wt % poly(ethylene terphthalate) (PET) and 40 wt % Abaca pulp fibers. The substrate was dried in an oven at 75° C. An add-on of between 20–25 wt % was achieved. The bound material was a little stiffer than the substrate due to the high $T_g$ (~140° C.) of PNiPAm. A 1"×1" piece of this material was placed in a scintillation vial in cold water and shaken vigorously on a shaker (from Eberbach Corporation). The material dispersed within 10 seconds. However, on shaking a similar sample vigorously in warm water (~40° C.) for over 10 minutes, this material did not lose integrity. The material begins to hydrate and disperse as the temperature cools to about 33.5° C. The cloud point of PNiPAm is 34° C.

EXAMPLE 7

N-isopropyl acrylamide (NiPAm) and N-tert-butylacrylamide (TBAM) monomers were copolymerized to produce a copolymer having 96 mole % NiPAm structural units and 4 mole % TBAM structural units. A 20–25 weight percent add-on of a 3 to 3.5 wt % binder solution of the copolymer was applied to a fibrous substrate. The substrate was a wet-laid nonwoven made from 0.5", 3 denier fibers wherein the fibers comprised 60 wt % poly(ethylene terphthalate) (PET) and 40 wt % Abaca pulp fibers.

The binder-containing substrate remained stable in warm water, but disperse within 10 seconds in cold water (31.5° C.) with agitation. The TBAM component of the binder lowered the cloud point of the polymer to 32.0° C.

EXAMPLE 8

N-isopropyl acrylamide (NiPAm) and N-tert-butylacrylamide (TBAM) monomers were copolymerized to produce a copolymer having 92 mole % NiPAm structural units and 8 mole % TBAM structural units. A 20–25 weight percent add-on of a 3 to 3.5 wt % binder solution of the copolymer was applied to a fibrous substrate. The substrate was identical to the substrate in Example 7.

The binder-containing substrate remained stable in warm water, but disperse within 10 seconds in cold water (28.5° C.) with agitation. The TBAM component of the binder lowered the cloud point of the polymer to 29.0° C.

EXAMPLE 9

PNiPAm was blended with 30 wt % poly(vinyl acetate) (PVAc) from a common solvent, methanol. The PVAc was a surfactant-free PVAc (VINAC® B-15 from Air Products). 20–25 weight percent add-on of a 3 to 3.5 wt % solution of PNiPAm/PVAc in methanol was applied to a fibrous substrate identical to the substrate of Example 7. The fibrous substrate retained its integrity in warm water (>34° C.), but dispersed in cold water (<33.5° C.) within 10 seconds. The triggering temperature, 33.5° C., was unaffected by the PVAc, since the temperature triggering is determined by the PNiPAm part of the binder formulation.

EXAMPLE 10

Example 9 was repeated except PNiPAm was blended with 60 wt % poly(vinyl acetate) (PVAc). The fibrous substrate retained its integrity in warm water (>34° C.), but dispersed in cold water (<33.5° C.) within 60 seconds. Again, the triggering temperature, 33.5° C., was unaffected by the PVAc.

The above disclosed examples are preferred embodiments and are not intended to limit the scope of the present invention in any way. Various modifications and other embodiments and uses of the disclosed NiPAm polymers, apparent to those of ordinary skill in the art, are also considered to be within the scope of the present invention.

What is claimed is:

1. A method of making a polymer comprising:
   forming an intermediate salt from a reaction mixture comprising polyacrylic acid and isopropylamine; and
   conducting a condensation reaction to convert the salt to the polymer and water.

2. The method of claim 1, wherein the method is a continuous extrusion process.

3. The method of claim 2, wherein one or more alcohols are injected into the reaction mixture during the continuous process to produce a copolymer or terpolymer of isopropyl acrylamide and at least one alkyl acrylate.

4. The method of claim 2, wherein N-tert-butylamine is injected into the reaction mixture during the continuous extrusion process.

5. The method of claim 1, wherein the intermediate salt comprises isopropylammonium polyacrylate salt.

6. The method of claim 1, wherein the polyacrylic acid is reacted with isopropylamine without solvent or with a polar solvent.

7. The method of claim 6, wherein the polar solvent comprises water, methanol, ethanol, or a combination thereof.

8. The method of claim 1, wherein the polyacrylic acid has an average molecular weight ranging from about 2,000 to about 5,000,000 grams/mole.

9. The method of claim 1, wherein the polyacrylic acid has an average melt flow index of from about 0.1 to 500 g/10 min. at about 230° C.

10. The method of claim 1, wherein the polymer produced from the method is free from residual monomers.

11. The method of claim 1, wherein a stoichiometric amount of isopropylamine is reacted with the polyacrylic acid.

12. A method of making poly(N-isopropyl acrylamide) comprising:
   forming an intermediate salt from a reaction mixture consisting essentially of polyacrylic acid and isopropylamine;
   conducting a condensation reaction to convert the salt to poly(N-isopropyl acrylamide) and water.

13. The method of claim 12, wherein the method is a continuous extrusion process.

14. The method of claim 12, wherein the poly(N-isopropyl acrylamide) produced from the method is free from residual monomers.

15. The method of claim 12, wherein a stoichiometric amount of isopropylamine is reacted with the polyacrylic acid.

16. A method of making a polymer in a continuous extrusion process, the method comprising:
   feeding a polyacrylic acid melt into an extruder;
   injecting a stream of isopropylamine into the polyacrylic acid melt;
   forming an intermediate salt from the polyacrylic acid and the isopropylamine in a first reaction zone of the extruder;
   converting the salt to the polymer and water in a second reaction zone of the extruder; and
   removing the water from a final zone of the extruder.

17. The method of claim 16, wherein the intermediate salt comprises isopropylammonium polyacrylate salt.

18. The method of claim 16, wherein the polyacrylic acid has an average molecular weight ranging from about 2,000 to about 5,000,000 grams/mole and an average melt flow index of from about 0.1 to 500 g/10 min. at about 230° C.

19. The method of claim 16, wherein the polymer is poly(N-isopropyl acrylamide).

20. The method of claim 16, wherein one or more alcohols are injected into the polyacrylic acid/isopropylamine mixture during the continuous extrusion process to produce the polymer.

21. The method of claim 16, wherein N-tert-butylamine is injected into the polyacrylic acid/isopropylamine mixture during the continuous extrusion process.

22. The method of claim 16, wherein the poly(N-isopropyl acrylamide) produced from the method is free from residual monomers.

23. The method of claim 16, wherein a stoichiometric amount of isopropylamine is reacted with the polyacrylic acid.

24. A method of making a polymer in a continuous extrusion process, the method comprising:
   forming an intermediate salt from a reaction mixture comprising polyacrylic acid and isopropylamine; and
   conducting a condensation reaction to convert the salt to the polymer and water;
   wherein a stream of isopropylamine is injected into a melt phase of the polyacrylic acid as the reaction mixture moves through an extruder.

25. The method of claim 24, wherein the intermediate salt is formed in a first reaction zone of the extruder.

26. The method of claim 25, wherein the intermediate salt is further extruded to decompose into poly(N-isopropyl acrylamide) and water and wherein the water is removed from a last section of the extruder.

27. A method of making poly(N-isopropyl acrylamide) comprising:
   forming an intermediate salt from a reaction mixture comprising polyacrylic acid and isopropylamine; and
   conducting a condensation reaction to convert the salt to poly(N-isopropyl acrylamide) and water.

* * * * *